(12) United States Patent
Carrieri et al.

(10) Patent No.: US 9,322,768 B1
(45) Date of Patent: Apr. 26, 2016

(54) SENSOR SYSTEM AND METHOD FOR THE PANORAMIC STANDOFF DETECTION OF CHEMICAL CONTAMINANTS ON TERRESTRIAL SURFACES

(71) Applicant: U.S. Army Research Development and Engineering Command, APG, MD (US)

(72) Inventors: Arthur H. Carrieri, Abingdon, MD (US); Tudor N. Buican, Albuquerque, NM (US); Erik S. Roese, Baltimore, MD (US); James Sutter, Tucson, AZ (US); Alan C. Samuels, Havre de Grace, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 445 days.

(21) Appl. No.: 13/796,166

(22) Filed: Mar. 12, 2013

(51) Int. Cl.
*G01N 21/23* (2006.01)
*G01N 21/27* (2006.01)
*G01N 21/71* (2006.01)

(52) U.S. Cl.
CPC .............. *G01N 21/27* (2013.01); *G01N 21/71* (2013.01)

(58) Field of Classification Search
CPC ............. G01N 2021/0125; G01N 2021/398; G01N 2021/1296; G01N 21/23; G01N 21/25; G01N 21/27; G01N 21/71; G05B 13/027; G05B 13/0275; G01J 3/447; G01J 3/45; B01B 9/02; B01B 9/02001; B01B 9/0203
USPC ................ 250/338.1, 339.07, 339.08, 341.1, 250/341.6, 352, 339.12; 356/491, 451, 453, 356/365; 706/15, 25, 48, 20, 41, 52
See application file for complete search history.

(56) References Cited

U.S. PATENT DOCUMENTS

| | | | | |
|---|---|---|---|---|
| 3,977,787 A | * | 8/1976 | Fletcher et al. | 356/451 |
| 5,553,616 A | * | 9/1996 | Ham et al. | 600/316 |
| 5,631,469 A | * | 5/1997 | Carrieri et al. | 250/341.5 |
| 5,659,391 A | * | 8/1997 | Carrieri | 356/451 |
| 5,708,503 A | * | 1/1998 | Carrieri | 356/453 |
| 6,060,710 A | * | 5/2000 | Carrieri et al. | 250/338.1 |
| 6,389,408 B1 | * | 5/2002 | Carrieri | 706/48 |
| 6,464,392 B1 | * | 10/2002 | Carrieri et al. | 374/45 |

(Continued)

OTHER PUBLICATIONS

Buican et al., Ultra-high speed solid-state FTIR spectroscopy and applications for chemical defense, Ft. Belvoir Defense Technical Information Center Dec. 2004.*

(Continued)

*Primary Examiner* — David Porta
*Assistant Examiner* — Djura Malevic
(74) *Attorney, Agent, or Firm* — Ulysses John Biffoni

(57) ABSTRACT

A pseudo-active chemical imaging sensor including irradiative transient heating, temperature nonequilibrium thermal luminescence spectroscopy, differential hyperspectral imaging, and artificial neural network technologies integrated together. The sensor may be applied to the terrestrial chemical contamination problem, where the interstitial contaminant compounds of detection interest (analytes) comprise liquid chemical warfare agents, their various derivative condensed phase compounds, and other material of a life-threatening nature. The sensor measures and processes a dynamic pattern of absorptive-emissive middle infrared molecular signature spectra of subject analytes to perform its chemical imaging and standoff detection functions successfully.

16 Claims, 6 Drawing Sheets

(56) References Cited

U.S. PATENT DOCUMENTS

| | | | |
|---|---|---|---|
| 6,587,600 B1* | 7/2003 | Shipley | 382/284 |
| 6,731,804 B1* | 5/2004 | Carrieri et al. | 382/191 |
| 7,038,789 B1* | 5/2006 | Carrieri | 356/491 |
| 7,262,414 B1* | 8/2007 | Carrieri et al. | 250/341.6 |
| 7,737,399 B1* | 6/2010 | Carrieri et al. | 250/338.1 |
| 8,406,859 B2* | 3/2013 | Zuzak et al. | 600/476 |
| 8,514,392 B1* | 8/2013 | Carrieri et al. | 356/322 |

OTHER PUBLICATIONS

Carrieri et al., Infrared differential-absorption Mueller matrix spectroscopy and neutral network-based data fusion for biological aerosol standoff detection, Applied Optics, vol. 49, No. 3, Jan. 2010.*

Carrieri et al. Surface contamination detection by means of near-infrared stimulation of thermal luminescence, Applied Optics, vol. 45, No. 4, Feb. 2006.*

Carrieri et al. Chemical imaging sensor and laser beacon Applied Optics vol. 42, No. 15 May 20, 2003.*

* cited by examiner

SENSOR SYSTEM AND METHOD FOR THE PANORAMIC STANDOFF DETECTION OF CHEMICAL CONTAMINANTS ON TERRESTRIAL SURFACES

GOVERNMENT INTEREST

The invention described herein may be manufactured, used, and/or licensed by or for the United States Government.

BACKGROUND

1. Technical Field

The embodiments herein generally relate to chemical detection technology, and more particularly to chemical imaging of suspect chemically contaminated surfaces and standoff detection of subject chemical contaminants.

2. Description of the Related Art

A variety of systems and methods have been developed and used to detect and identify hazardous chemical and biological threat agents in the field. Chemical test kits that employ chemically reactive vapor-samplers and detection papers have long been used to detect chemical nerve agents, blood agents, and blister agents. While chemical kits are generally useful, they are designed to detect a limited range of conventional chemical agents that are toxic in the range of $10^{-3}$ g/person, provide no standoff protection, and may be prone to false negative and positive detections.

Systems that employ Ion Mobility Spectrometry (IMS) in which molecules are ionized and separated according to their differences in velocities through a gas in the presence of an electric field can, in theory, identify and detect a wide variety of chemical and biological warfare (CBW) agents. IMS systems, however, require direct exposure to the chemical agent and the instruments typically have insufficient resolving power to identify CBW agents before they have reached casualty producing levels.

Other systems employ passive infrared (PIR) imaging to detect airborne chemical threats such as nerve (GA, GB, and GD) and blister (H and L) agents based on the infrared spectrum of the agent. Currently fielded devices have been reported to detect aerosols at a distance of up to 5 km. Practical PIR detection systems have difficulty detecting low levels of CBW surface target contaminants because the surfaces are typically at thermal equilibrium and provide insufficient contrast to identify target contaminants. Additionally, background radiation and interference encountered in the field can also make detection difficult.

U.S. Pat. Nos. 5,241,179; 5,708,503; 6,464,392; 6,731,804; 7,038,789, and 7,262,414, the complete disclosures of which, in their entireties, are herein incorporated by reference, provide technologies for chemical threat detection. However, as threats continue to become more sophisticated, enhanced techniques are needed to provide suitable detection capabilities.

The U.S. military seeks, develops, and tests promising technologies capable of solving complex tactical standoff detection problems at a safe range. Scenarios of interest include chemical warfare agents (CWAs) in vapor/aerosol forms released into the open atmosphere vis-à-vis ordinance discharge, and surface contamination resulting from deposition and settling of the aerosol mass onto/into porous soil, sand, roads, bridges, etc. Accordingly, it would be advantageous to develop a sensor applied specifically to these problems.

SUMMARY

In view of the foregoing, the embodiments herein provide a pseudo-active chemical imaging sensor including irradiative transient heating, temperature nonequilibrium thermal luminescence spectroscopy, differential hyperspectral imaging, and artificial neural network technologies integrated together. The sensor may be applied to the terrestrial chemical contamination problem, where the interstitial contaminant compounds of detection interest (analytes) comprise liquid chemical warfare agents, their various derivative condensed phase compounds, and other material of a life-threatening nature. The sensor measures and processes a dynamic pattern of absorptive-emissive middle infrared molecular signature spectra of subject analytes to perform its chemical imaging and standoff detection functions successfully.

A chemical imaging sensor is provided for detecting and imaging chemical contaminants comprising analytes, the sensor comprising a first component that performs irradiative transient heating; a second component that performs temperature nonequilibrium thermal luminescence spectroscopy; a third component that performs differential hyperspectral imaging; and a fourth component that performs artificial neural networking, wherein the first, second, third, and fourth component combine to measure and process a dynamic pattern of absorptive-emissive middle infrared molecular signature spectra of the analytes.

The sensor further comprises a spectroradiometer receiver; and a laser transmitter comprising a waveguide laser emitting a linearly-polarized continuous-wave (cw) beam in a stable transverse electromagnetic wave spatial mode comprising energy that is absorbing to the chemical contaminants and lies outside an optical bandwidth of the spectroradiometer receiver. The laser transmitter further comprises a stress-birefringence photoelastic modulator (PEM) aligned 45° to the beam producing an incident polarization-modulation beam (iPM-beam); and a beam expander (BF) that expands the iPM-beam and reduces a divergence of the iPM-beam.

The laser transmitter further comprises a mirror; a raster scanner assembly (SA) that drives the mirror in azimuth angles $\phi$ and polar angles $\theta$ and directs the iPM-beam onto suspect areas containing the chemical contaminants inside a panoramic field-of-view of the spectroradiometer receiver; and a semi-shell entrance window that protects the waveguide laser, the PEM, the BE, the mirror, and the SA. The intensity of the iPM-beam is below a first threshold that causes charring of an irradiated surface comprising the chemical contaminants, and wherein the intensity of the iPM-beam is at or above a second threshold that is required to generate sufficient thermal luminescence fluxes.

The spectroradiometer receiver comprises an internal chamber; an entrance window that seals and protecting optic components within the internal chamber; and a vacuum pump-down valve operatively connected to the internal chamber. The spectroradiometer receiver further comprises a liquid nitrogen Dewar cryostat and a focal-plane array detector housed inside the Dewar cryostat that produces interferogram waveforms of imaged panoramic field-of-view (PFOV) thermal luminescence flux rays. The spectroradiometer receiver further comprises a collector optic component group comprising a plurality of hyperboloid mirrors. The spectroradiometer receiver further comprises a Schwarzschild objective collimator optics component group comprising a plurality of spherical mirrors.

The spectroradiometer receiver further comprises a stress-solid-state interferometer comprising front and back linear polarizers sandwiching a virtual stack phased-array (VSPA) bar photoelastic modulation (PEM), wherein the VSPA bar PEM comprises a single stress-birefringence ZnSe crystal having an array of ultrasonic-frequency piezoelectric transducers (PZTs) bonded across a length of the crystal, and wherein the VSPA bar PEM is activated by the PZTs generating interferograms at ultrahigh-speed on collimated panoramic field-of-view light incoming from the Schwarzschild objective collimator optics component group collected by the collector optic component group. The spectroradiometer receiver further comprises a lens imager component group that images interferometrically-processed PFOV rays of object space from the VSPA bar PEM onto the focal plane array detector.

Another embodiment includes a method of detecting and imaging chemical contaminants, the method comprising providing a sensor comprising a spectroradiometer receiver and a laser transmitter, emitting a linearly-polarized continuous-wave (cw) beam in a stable transverse electromagnetic wave spatial mode comprising energy that is absorbing to the chemical contaminants and lies outside an optical bandwidth of the spectroradiometer receiver, producing an incident polarization-modulation beam (iPM-beam) using a stress-birefringence photoelastic modulator (PEM) aligned 45° to the cw beam; expanding the iPM-beam; reducing a divergence of the iPM-beam; and directing the iPM-beam onto suspect areas containing the chemical contaminants inside a panoramic field-of-view of the spectroradiometer receiver.

The intensity of the iPM-beam is below a first threshold that causes charring of an irradiated surface comprising the chemical contaminants, and wherein the intensity of the iPM-beam is at or above a second threshold that is required to generate sufficient thermal luminescence fluxes. The spectroradiometer receiver comprises an internal chamber; an entrance window that seals and protecting optic components within the internal chamber; and a vacuum pump-down valve operatively connected to the internal chamber. The spectroradiometer receiver further comprises a liquid nitrogen Dewar cryostat; and a focal-plane array detector housed inside the Dewar cryostat that produces interferogram waveforms of imaged panoramic field-of-view (PFOV) thermal luminescence flux rays. The spectroradiometer receiver further comprises a collector optic component group comprising a plurality of hyperboloid mirrors. The spectroradiometer receiver further comprises a Schwarzschild objective collimator optics component group comprising a plurality of spherical mirrors.

The spectroradiometer receiver further comprises a stress-solid-state interferometer comprising front and back linear polarizers sandwiching a virtual stack phased-array (VSPA) bar photoelastic modulation (PEM), wherein the VSPA bar PEM comprises a single stress-birefringence ZnSe crystal having an array of ultrasonic-frequency piezoelectric transducers (PZTs) bonded across a length of the crystal, and wherein the VSPA bar PEM is activated by the PZTs generating interferograms at ultrahigh-speed on collimated panoramic field-of-view light incoming from the Schwarzschild objective collimator optics component group collected by the collector optic component group. The spectroradiometer receiver further comprises a lens imager component group that images the PFOV rays of object space onto the focal plane array detector.

The method further comprises measuring and processing a dynamic pattern of absorptive-emissive middle infrared molecular signature spectra of analytes of the chemical contaminants. Additionally, the method further comprises performing a genetic algorithm optimization of the spectroradiometer receiver and the laser transmitter.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION

Figure 1:
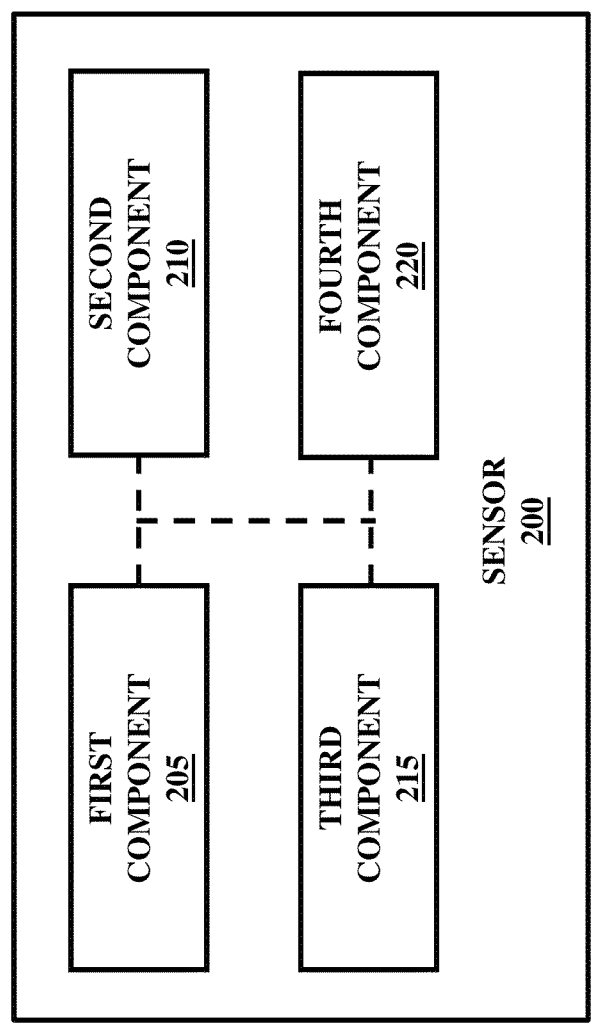
FIG. 1 illustrates a system block diagram of a sensor according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a pseudo-active chemical imaging sensor including irradiative transient heating, temperature nonequilibrium thermal luminescence spectroscopy, differential hyperspectral imaging, and artificial neural network technologies integrated together. Referring now to the drawings, and more particularly to FIGS. 1 through 6, where similar reference characters denote corresponding features consistently throughout the figures, there are shown preferred embodiments.

As mentioned, it would be advantageous to develop a sensor applied specifically to the various scenarios of interest described. The embodiments herein provide a sensor and technique to address this need. The development of the sensor provided by the embodiments herein initially involves conducting a phenomenological study of the CWA's atmospheric and/or surface environments, the mechanisms of analyte mass transportation, and the principles of analyte mass detection; i.e., light-matter interactions. This involves using a panoramic-imaging spectroradiometer (PANSPEC) system more specifically, a middle infrared (MIR) PANSPEC chemical cloud-imaging model (PCCM), which is further described in U.S. Pat. Nos. 5,708,503 and 7,038,789, the complete disclosures of which, in their entireties, are herein incorporated by reference. Various aspects of the PCCM and its concept of use are set forth as follows.

The PCCM prescribes collecting ambient MIR radiance stared at over its panoramic field-of-view (PFOV) object space consisting of the open atmosphere, collimating that radiance into a tight beam sent through an ultrahigh-speed (UHS) no moving parts solid-state interferometer, and imaging the interferometer exitance beam onto an image space occupied by a focal plane array (FPA) of n×n HgCdTe detector elements. Streaming $n^2$ interferogram voltage waveforms output by the FPA are digitized via high-speed electronics and converted into MIR spectral frames, which are subsequently mined for MIR molecular vibration/vibration-rotation resonance bands whose structure (frequencies and amplitudes of bands) correlate to the subject analyte mass (cloud's toxic chemical vapor/aerosol constituents) one-to-one. Expert artificial neural network (ANN) pattern recognition algorithms perform the spectral mining task.

The ANN recognizes signature molecular vibration/vibration-rotation bands of the analyte alternating between negative- and positive-parity amplitudes in difference-spectra, where parity is in reference to the baseline of difference-spectrum measurements. Negative-parity of spectral bands represent MIR radiance passed through the absorbing cloud and stimulating the analytes' molecular vibration/vibration-rotation states, and positive-parity of spectral bands represent those excited molecules returned to lower energy levels vis-à-vis Kirchoff's radiation law: good absorbers are good infrared emitters. Amplitudes of the ± molecular resonance bands change in relation to capacity of the analyte to gain heat via absorption of background solar radiance and lose heat by MIR emissions. Moreover, frequencies (energies) of molecular resonance bands are invariant as long as there is no dissociation amongst the molecular analytes' due to photofragmentation and/or chemical reactions. This facilitates the ANN algorithm locking into consistent detection metrics.

Accordingly, the PCCM conducts its aerosol/vapor chemical imaging and tracking steps as follows:

Step 1: Data Acquisition, Preprocessing, and Formatting

The UHS solid-state interferometer of the PCCM incorporates front and back linear-polarizer optics sandwiching three nearly identical stress-birefringence single-window photoelastic modulators (PEMs) generating transient hyperspectral images in the following context. First, a beam of radiance collected then collimated from the PCCM panorama (iPFOV-beam) is incident to the interferometer. The iPFOV-beam in its ambient random polarization state transforms to a linear-polarization state (lpPFOV-beam) on transmission through the front linear-polarizer optic. Second, the polarization axis of the lpPFOV-beam is oriented precisely 45° to the birefringence optical axis of the first birefringence ZnSe window element of the interferometer. Third, all three ZnSe window PEM elements of the interferometer with bonded with piezoelectric transductions (PZTs) are cyclically compressed-relaxed at their natural mechanical resonance frequency $v_r$~30 kHz (UHS designation), thereby transforming the lpPFOV-beam entering the 3-PEM crystals array into a polarization-modulation beam exiting that array (pmPFOV-beam). Fourth, the pmPFOV-beam transforms into an intensity-modulation beam (imPFOV-beam) upon transmission through the back linear-polarizer optic of the interferometer. Filth, a refractive lens elements group images the imPFOV-beam onto the FPA; the latter matched in size to panorama of PCCM. Sixth, electronic preamplification then digitization operators act simultaneously on $n^2$ voltage waveform outputs from the FPA (these waveforms were previously called interferograms) produced at the rate of $4v_r$ ($2v_r$ if the zero-retardation points of ZnSe PEM retarders double in retardation amplitude). Seventh, the latter streaming interferogram data strings are algorithmically time-stamped, grouped, co-added in groups of tens-to-hundreds producing sufficient signal-to-noise ratio, averaged, and fast Fourier transformed into running MIR spectra ($S_i$). Eighth, contiguous $S_i$ are subtracted and cast into data set $\{dS\}=\{S_r-S_{r-1} \forall r=2,3,\ldots s\}$, where $S_s$ is the final spectrum measured over the end PZT runtime period of the interferometer. Ninth, the family of curves in $\{dS\}$ transforms into a differential-hyperspectral imaging map (DHIM)

$$\mathscr{H} = \left\{ \sum_{i,j=1}^{n} dS(v, t; \omega_{i,j}) \right\},$$

υ spans the 833.3≤υ≤1250.0 cm-1 (spectroscopy wavenumber units) MIR optical bandwidth of interferometer, t is runtime of the interferometer in piezoelectric transduction, $\omega_{i,j}$ is instantaneous field of view of the (i,j) pixel of the FPA, and the summation is carried over all $n^2$ pixels covering the panorama of the PCCM.

Step 2: Data Filtration $\mathscr{H}$ is operated on by a multifilter algorithm that recursively filters noisy dS(υ; t; ωi,j) datastreams producing a statistically optimal signal-to-noise voltage ratio ($\mathscr{S}/\mathscr{N}$). Signal ($\mathscr{S}$) is the normalized absorption-emission MIR resonance spectral bands of analyte (above), and noise ($\mathscr{N}$) is everything else; e.g., multiple extended sources, spurious electrical pick-ups by data acquisition circuits of the sensor and the FPA's semiconductor pixel elements, etc.

Step 3: Pattern Recognition

Filtered $\mathscr{H}$ is preprocessed, formatted, multiplexed in affined slices of dS(υ; t; ωi,j), and then feed-forwarded through an ANN whose architecture accommodates the DHIM data structure. The former preprocessing algorithms comprise linear baseline correction, negative-to-positive spectra parity conversion, normalization, and data formatting operators. The latter ANN processor is a supervised-learning, backward-error propagation ("back prop") pattern recognition operator trained, tested, and validated against the spectrum detection metrics of known analyte(s), which is further described in U.S. Pat. No. 5,631,469, the complete disclosure of which, in its entirety, is herein incorporated by reference.

Step 4: Chemical Imaging Spectroscopy and Analyte Detection

Chemical imaging spectroscopy and analyte standoff detection are functions performed by the PCCM in which positive detection ANN events from step 3 are superimposed on the DHIM from steps 1-2.

Conventional vapor/aerosol standoff detection modeling efforts may be applicable to the surface contamination problem of chemical defense interest; namely, standoff surveillance of chemically contaminated terrain (CCT) in the battlefield. This tactical field scenario typically presents itself as a final fate of launched-then-detonated CWA ordinance whose payload comprises incapacitating and ultimately lethal nerve agent compounds such as VX (in the organophosphonothiolate class) and blister agent compounds such as Lewisite (in the organoarsenic class), their derivatives (molecular group substitutions), and thickened CWAs of such. On detonation of an ordinance shell its liquid payload disperses as a remnant CWA rain (large-sized droplets) that settle on land below the detonation locus, and as a remnant CWA aerosol cloud (lesser-sized droplets) that are transported by air currents to settle on a downwind surface area swath. Powdered and aerosolized biological warfare agent ordinance payloads present similar if not more potent threats.

The embodiments herein provide a PANSPEC surface contamination model (PSCSM) that overcomes the problems described above using, for example, coupled temperature nonequilibrium phenomena and thermal luminescence (TL) spectroscopy, including technologies described in U.S. Pat. Nos. 5,241,179, 6,464,392, and 7,262,414, the complete disclosures of which, in their entireties, are herein incorporated by reference. PSCSM and PCCM are similar, with the former encompassing several enhancements and additions including: a virtual stack phased-array (VSPA) interferometer for producing high-resolution DHIMs in very short timeframes (milliseconds); a directed laser transmitter for rapidly pumping TL fluxes from suspect CCT; a modified MIR imager re-optimized for clear demagnified imagery; an unsupervised self-organization map (SOM) pattern recognition and clustering algorithm for deciding on presence/absence of the CWA surface contaminants; and other modifications.

The unsupervised SOM ANN implements reinforcement competitive learning via a topology-preserving nonlinear clustering map algorithm that passes DHIM data (steps 1 and 2) from its input space of linear nodes (also called processing elements or neurons) onto its output space of latticed nodes. Locations of the neurons so tuned on the discretized output space lattice are 'winning neurons': they form the topological map. In accordance with the embodiments herein, the algorithm adjusts weights as "distances" computed between exemplars in a 208-D linear input space representing 208 coordinates of dS($\upsilon$) of 2 cm$^{-1}$ resolution, to "codebook vectors" organized in a 2-D discretized output space where clustering of the CWA surface contaminant analyte is most readily visualized and interpreted (steps 3 and 4). The ability to cluster is a manifestation of the molecular vibration resonance moieties (identification cues) of analyte inherited in dS($\upsilon$) measurements (steps 2-3). The molecular species of CWAs possessing strong fingerprint spectra that are unknown or unavailable, such as derivative CWA compounds that may have equal or greater toxicity then their parent, are subject to clustering. Clustering is the sole requirement of CWA standoff detection; an extraordinary capability for detecting both known and unknown analytes.

TLS Surface Contamination Detection

Irradiative transient heating (ITH) is the transfer of energy to and from a body by means of absorption and emission of electromagnetic radiation. ITH conveys TL fluxes generated, acquired, and analyzed accordingly: boost the suspect CCT into temperature nonequilibrium via irradiation from, for instance, a 0.102 eV photon energy (also 826 cm$^{-1}$ spectroscopy units $\upsilon$, and 12.1 μm wavelength units $\lambda$)$^{14}$CO$_2$ laser beam (iPM-beam); interferometrically process the concomitant CCT-to-ambient TL flux radiance (step 1 above); transform these data into a hyperspectral data cube $\mathcal{H}$ (steps 2-3 above); and mine $\mathcal{H}$ for the subject analytes' signature molecular vibration/vibration-rotation bands (step 4 above).

The Gaussian iPM-beam heating source exhibits strong absorption cross-section $\Pi(\nu)$ defined as the ratio of the amount of field energy removed from the iPM-beam into the CCT material to the beam's total incident energy $\upsilon$=826 cm$^{-1}$. Here, $\upsilon$ lies just outside the 833.3-1250.0 cm$^{-1}$ bandwidth of spectroradiometer measuring TL fluxes, thus identifying TLS standoff detection technology as pseudo-active. If the iPM-beam energy were tuned inside 833.3-1250.0 cm$^{-1}$, then a blinding scattered-beam radiance corona flushes the weak molecular absorptive-emissive resonance bands spectral features carried in the liberated TL fluxes. Moreover, the iPM-beam is preferably polarization-modulated since absorption cross section ($\Pi$) is slightly polarization (P) and polarization-modulation ($\dot{P}$) dependent. This phenomenon was observed in experiments, where iPM-beam irradiated CCT at $\dot{P}$=32 kHz in comparison to $\dot{P}$=0 (fixed linear-polarization laser beam) boosts TL flux radiance by approximately 5%, which is further described in U.S. Pat. No. 5,241,179, the complete disclosure of which, in its entirety, is herein incorporated by reference. That implies preferential absorption in the CCT medium by the iPM-beam's swept continuum of (+/−) linear-elliptical-circular polarization states, with the desirable effect of increasing $\mathcal{S}/\mathcal{N}$ in DHIMs (step 2 above). One can exploit the polarization-modulated beam absorption cause and thermal luminescence fluxes TL($\dot{P}$) effect relationship of ITH by sweeping at various values and discerning one or more frequencies of modulation causing TL($\dot{P}$) to peak. For example, one may conduct an optimization experiment whereby dS are measured (step 1 above) for an iPM-beam of $\dot{P}$=0, (constant linear or random polarization) and $\dot{P}$=10$^3$ (swept polarization states per s) in $\dot{P}$ steps of 1 kHz. Analyses of $\mathcal{H}$ (step 4 above) as a function of $\dot{P}$ may provide clues toward understanding the $\Pi(\lambda,P;\dot{P})$ mechanism and help establish optimum design parameters for the sensor of FIG. 2. Finally, the iPM-beam is dither-stabilized in the spatial transverse electromagnetic wave mode TEM$_{00}$ (uniform disk intensity), and that intensity pumps adequate TL fluxes for detection purposes yet below what would cause the CCT to char or burn; 10-50 Wcm$^{-2}$ is typical for TLS standoff detection at ranges of 5-20 m, respectively.

The iPM-beam pumping of TL fluxes from the CCT (a composite inhomogeneous dielectric medium comprising of strata and contaminant boundary layers randomly distributed) stimulates a pattern of closely associated surface temperature gradients ($\nabla T$) and emissivity contrasts ($\partial \in /\partial T$) evolving between the CCT's dissimilar dielectric layers. These $\nabla T$ and $\partial \in /\partial T$ thermodynamic events rise in phase with each other upon incident iPM-beam exposure, continue to build then peak at some iPM-beam irradiation time ($t_p$) when the CCT is in its most advanced thermal nonequilibrium state, and decline toward a near null as the CCT returns to thermal pseudo-equilibrium at elevated temperature with a small temperature oscillation. They can be tracked by a PSCSM-based system measuring a family of graybody emissions spectra G(T, $\upsilon$, t); emissivity; $\in$=1 for a perfect Planck blackbody object, $0 \le \in < 1$ for terrestrial graybody objects, increasing in amplitudes and up-shifting in frequencies during ITH), which is further described in U.S. Pat. Nos. 5,241,179, 6,464,392, and 6,731,804, the complete disclosures of which, in their entireties, are herein incorporated by reference. The period of iPM-beam irradiation in the $\partial^2 G(T, \upsilon, t)/\partial \upsilon \partial t|_{t=t_p}$=0 neighborhood is referred to as a 'detection window of opportunity' (WDO) wherein $\nabla T$ and $\partial \in /\partial T$ have peaked. The intelligent PSCSM-based prototype system monitors WDO conditions and collects $\mathcal{H}$ data within the WDO via two logical modes of operations: a 'background mode' continually measuring G(T, $\upsilon$, t; $\omega_{i,j}$) [assume dS($\upsilon$; t; $\omega_{i,j}$)=dG($\upsilon$; $T_s(t)$; $\omega_{i,j}$)], and a chemical imaging mode producing DHIMs gated inside the WDO (steps 1-4 above). For example, in a tactical field maneuver the deployed PSCSM-based sensor chemically images interstitial layers of nerve CWA VX=O-ethyl S-[2(diisopropylamino)ethyl]methyl phosphonothioate wetting sand, or any lossy, solid, inhomogeneous dielectric medium. VX is a high viscosity, non-volatile, extremely toxic liquid with motor oil-like rheology outlawed by the Chemical Weapons Convention of 1993. Generally, VX serves only one purpose, as a weapon of mass destruction. The sensor must separate weak yet sharp molecular resonance bands of VX (a P—$CH_3$ rocking normal mode of motion at energy 894 $cm^{-1}$ and a P—O—C stretching normal mode of motion at energy 1036 $cm^{-1}$) from the dominant, broad, and ubiquitous Restrahlen emission band of sand.

TL radiometric spectral band signal intensities ($I_{sig}$) of DMMP, DIMP, and SF96 can be observed at approximately the 5 parts per thousand level in reference to the broadband Restrahlen emission band intensity (ICCT); i.e., $I_{sig}/I_{CCT}$~0.005. $I_{sig}$ is superimposed on $I_{CCT}$ over the entire temporal window of observation ($I_{CCT}$ is the carrier of $I_{sig}$), however, spectral bands of the analyte in $I_{sig}$ are observable only in the short WDO timeframe. It can be concluded from these experiments that boosting $\mathcal{S}/\mathcal{N}$ by orders of magnitude is necessary for producing viable CCT standoff detection DHIMs (step 4 above). Ergo, a very high rate of interferogram data acquisition (Θ in interferograms per second) is helpful, as S/N is proportional to the number of co-added interferograms to the ½ power. An interferometer operating at $\Theta^{-1}$ greater than or about the WDO timeframe has a low probability of detecting and resolving the transitioning absorption-emission spectral bands of analytes in $\mathcal{H}$ (step 1 above). If $\Theta^{-1}$ is approximately in the range of half to a tenth of the WDO timeframe, then the analyte's transitioning absorption-emission molecular resonance bands of opposite amplitudes can average and null in the dG(T, υ, t contained in the WDO; $\omega_{i,j}$) measurement. Therefore, the interferometer should acquire data in timeframe $\Theta^{-1}$<<WDO capturing the absorption-emission bands transients of analyte with adequate temporal resolution.

Continuing constant-intensity iPM-beam irradiation beyond the WDO eventually brings the VX-sand medium back to thermal pseudo-equilibrium at elevated temperature, whereupon ∇T and ∂∈/∂T had already collapsed and the detection metric of VX sank into a noise abyss of dG(T, υ, $t>t_{stop}$), whereby $t_{stop}$ is the WDO closure time set by the PSCSM-based prototype system running in its background mode detecting sufficiently small threshold values of ∇T and ∂∈/∂T.

FIG. 1 illustrates a system block diagram of a chemical imaging sensor 200 for detecting and imaging chemical contaminants comprising analytes (not shown), the sensor 200 comprising a first component 205 that performs irradiative transient heating; a second component 210 that performs temperature nonequilibrium thermal luminescence spectroscopy; a third component 215 that performs differential hyperspectral imaging; and a fourth component 220 that performs artificial neural networking, wherein the first, second, third, and fourth components 205-220 combine to measure and process a dynamic pattern of absorptive-emissive middle infrared molecular signature spectra of the analytes.

PSCSM Transmitter and Zonal ITH:

FIG. 2, with reference to FIG. 1, illustrates a cut-away view of a laser transmitter component 10 of a surface contamination sensor model PSCSM (e.g., sensor 200). A $^{14}CO_2$ waveguide laser (L) 15 emits a continuous-wave 0.102 eV energy beam 20 that is linear-polarized and stable in the $TEM_{00}$ spatial mode (L-beam). A stress-birefringence photoelastic modulation (PEM) ZnSe crystal 25 is aligned precisely 45° to the incident linear-polarized L-beam, producing an incident Gaussian polarization-modulation beam (iPM-beam) 30 onto subject chemical contaminated terrain (CCT). A beam expander (BE) 35 reduces iPM-beam divergence. A raster scanner assembly (SA) 40 includes a flat mirror (M) 45 in azimuth (ϕ) and polar angle (θ) and facilitates iPM-beam area-heating of the CCT. A Ge hemispherical shell window of transmitter ($W_t$) 50 may be configured as a dust cover and protector of the laser 15, PEM ZnSe crystal 25, BE 35, and SA 40.

The iPM-beam 30 is polarization-modulated at $\dot{P}=\nu_{PEM}$ when traversed through PEM 25 (45° alignment between the linear polarization axis of the beam output by the laser 15 and the birefringence axis of the PEM 25 is assumed for full polarization-modulation of the beam 30). The BE 35 may be configured as a 10× beam expander used to decrease divergence of the iPM-beam 30 sent to the SA 40. The SA 40 is comprised of electromechanical actuators SAϕ and $SA_\theta$ that drive the high-reflectance flat mirror 45, project the expanded and highly collimated iPM-beam 30 onto suspect CCT inside the PFOV of spectroradiometer. Beam projections correspond to four distinct CCT area-heating case modes. Case 1 is for TL imaging over a full PFOV subtended onto the CCT; i.e., SAϕ and $SA_\theta$ rapidly raster-scans the iPM-beam over an annular area surrounding the sensor. Case 2 is for TL imaging over a segment of the PFOV (subannulus area); i.e., SAϕ oscillates in bounded azimuth angle ϕ while $SA_\theta$ oscillates in polar angles 0.39π≥θ≥0.20π rad covering the subannulus area of panorama. Case 3 is for TL imaging over a radial line segment of the PFOV annulus area; i.e., fixed SAϕ while SAO rapidly oscillates between 0.39π≥θ≥0.20π rad. Finally, Case 4 is for spot imaging inside the panorama; i.e., fixed SAϕ and $SA_\theta$. Cases 1 through 4 enact sequentially by the PSCSM when triangulating for detection events.

Antireflection coatings may be configured on the inner and outer surfaces of the hemispherical shell $W_t$ 50 assuring maximum transmission of the iPM-beam 30 through it. Furthermore, radii of curvatures of both surfaces of the hemispherical shell $W_t$ 50 are coincident at the center of the mirror 45, as this assures nil path-length deviation of iPM-beam-onto-CCT. Finally, the outer surface of the hemispherical shell $W_t$ 50 contains a hydrophobic film so that the sensor can operate in high humidity external environments.

PSCSM Spectroradiometer Receiver:

FIG. 3, with reference to FIGS. 1 and 2, illustrates a schematic diagram of a spectroradiometer receiver component 60 of the PANSPEC surface contamination sensor model PSCSM. A Ge hemispherical shell entrance window 65 seals of the internal chamber 75 of the spectroradiometer 60 and protects the corresponding internal optics. A vacuum pump-down valve 70 is provided for evacuating the internal chamber 75. Additionally, a focal-plane array (FPA) detector 80 is housed inside a windowed liquid nitrogen Dewar cryostat 85. A collector-focuser (CF) optic component group 90 is provided and comprises hyperboloid mirrors 91*a*, 91*b*. A Schwarzschild objective collimator optics component group 92 is provided and comprises two spherical mirrors 93*a*, 93*b*. A virtual stack phased-array (VSPA) bar photoelastic modulator 94 is provided along with a 5-lens imager 95*a*-95*k*, of which the final two aft lens imager lens 95*h*-95*k* are shown in system 95 with traced throughput rays onto the FPA detector 80.

The environment of the low-vacuum internal chamber 75 facilitates precise DHIM measurements by maintaining stable shapes and alignments of the sensor's internal optics as pressure and temperature fluctuate in the external ambient environment. Moreover, the internal chamber vacuum prevents air breakdown at deep focus of PFOV radiance via the collector-focuser 90.

The FPA 80 of the spectroradiometer 60 is nominally composed of small semiconductor HgCdTe photoconductive pixel elements embedded on a metalized contact pad, oriented in an n×n array, and housed within the MIR-windowed Dewar cryostat 85 that is also pumped-down to low vacuum. The HgCdTe photoconductive pixel elements of the n×n array are in contact with liquid nitrogen, cooling them to 77 K, decreasing their intrinsic thermal noise levels, and therefore increasing photonics sensitivity of the FPA by orders of magnitude. The FPA photonics signal outputs are comprised of $n^2$ independent voltage waveforms (interferograms) generated in the following context: the imaged imPFOV-beam promotes free electron-hole carrier pairs (EHCPs) in illuminated $n^2$ HgCdTe pixel elements; the rate of EHCPs generated is proportional to surface conductivity rate of change $\dot{\sigma}_c(t)$ in the HgCdTe semiconductor material; i.e., $\dot{\sigma}_c(t) \propto$ EHCP; each HgCdTe pixel element is connected in series to a bias voltage and load resistor circuit; and $(v_{11}(t), v_{12}(t) \ldots v_{nn}(t))$ are interferograms measured across the load resistors of respective arrayed HgCdTe pixel circuits processed as described in step 1 above.

Figure 3:
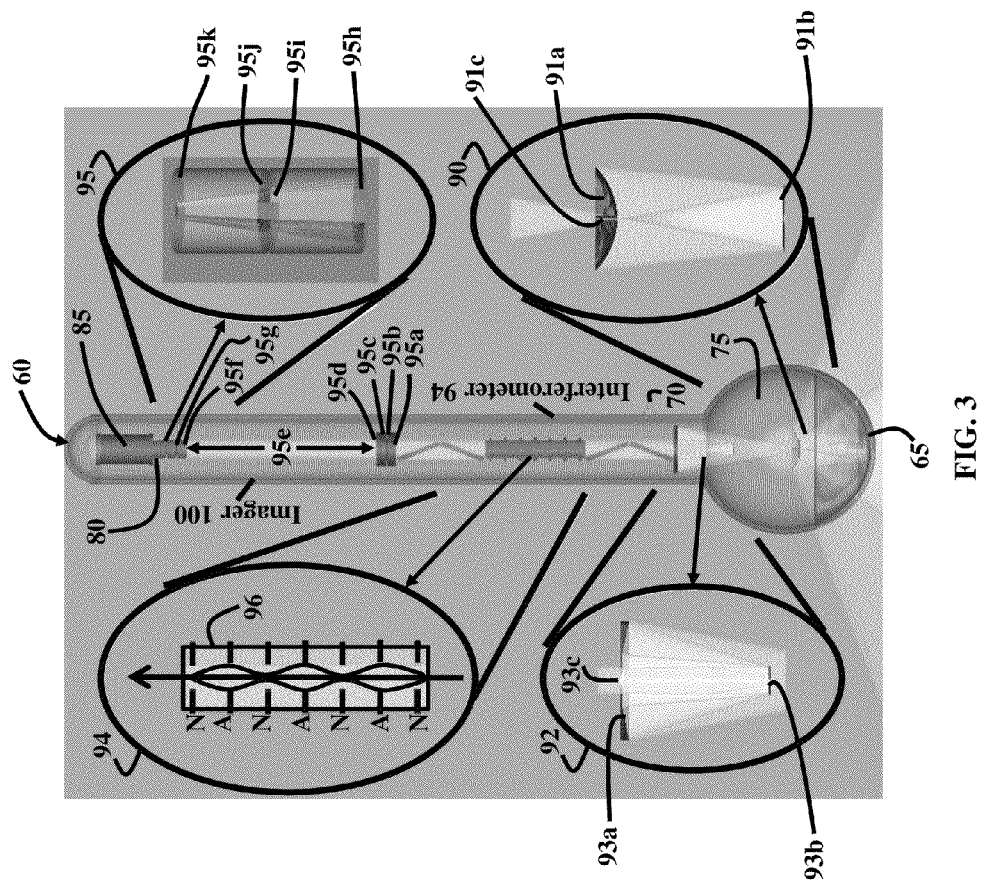
FIG. 3 illustrates a schematic diagram of a spectroradiometer receiver according to an embodiment herein.

Hemispherical Shell Entrance Window:

FIG. 3 shows the Ge hemispherical shell entrance window 65 whereby Ge is a natural MIR optical band-pass filter. The radii of curvatures and the inner- and outer-surfaces of the window 65, respectively, are concentric at the entrance pupil (EP) center. The EP is the vignetted image of the spectroradiometer's aperture stop, as viewing FIG. 3 on axis from object space $\Omega = \int_0^{2\pi} \int_{0.20\pi}^{0.39\pi} \sin\sigma d\sigma d\phi' = 0.93\pi$ sr [Note: upper limit on first(second) integral is $2\pi(0.39\pi)$]; where $\sigma$ and $\phi'$ are the spherical polar and azimuth angles of that space. Vignetting is distortion of the EP from true paraxial imaging. The EP dictates spectroradiometer MIR radiance throughput. This configuration of the window 65 assures nil optical path-length difference of chief rays passing through it from $\Omega$, which implies the window 65 is aberration-free. Moreover, the window 65 possesses antireflection-coatings on its inner and outer surfaces for maximum transmission of MIR $\Omega$ field rays, and a thin index-matched hydrophobic coating preserves fidelity of DHIM measurements when operating the PSCSM-based system in humid field environments.

Reflective Collector-Focuser:

The collector-focuser 90 is comprised of primary and secondary hyperboloid mirrors 91a, 91b. The collector-focuser 90 collects and focuses MIR $\Omega$-radiance on the center of the aperture stop (AS) 91c with diffraction-limited spot size. The AS may be configured with a 2.6325 mm semi-diameter, in one example. The primary convex hyperboloid mirror 91a, with a small-bore hole through its vertex, reflects-converges incoming $0.93\pi$ sr $\Omega$-radiance onto secondary concave hyperboloid mirror 91b that retroreflects and focuses that radiance back onto the vertex of 91a where iris AS 91c is located. The maximum diameter of iris AS 91c matches the bore diameter of mirror 91a. Imaging can be sharpened by stopping-down the spectroradiometer 60; i.e., reducing the opening of iris 93c positioned just after the collimator 92, followed by a compensatory reducing of diameter of AS 91c. There are two optical constraints imposed on the CF 90: a focus constraint $\overline{A_5 f_5} = s$; where $\overline{A_5 f_5}$ is the focal length of mirror 91b on its concave side and s is axial displacement between mirror 91a and mirror 91b; and a confocal constraint, where $\overline{A_4 f_4'} = s + \overline{A_5 f_5'}$; where $\overline{A_4 f_4'}(\overline{A_5 f_5'})$ is the focal length distance of mirror 91a (mirror 91b) on its convex (convex) side. Algebraic manipulation of the above two constraint relationships derives the CF optimization equation:

$$p_4 \left( \frac{\zeta_5 - 1}{\zeta_4 - 1} \right) - s(\zeta_5 - 1) = p_5; \qquad (1)$$

where $p_4$ and $p_5$ ($\zeta_4$ and $\zeta_5$) are radii of curvature (eccentricities) of mirrors 91a, 91b, respectively.

Figure 2:
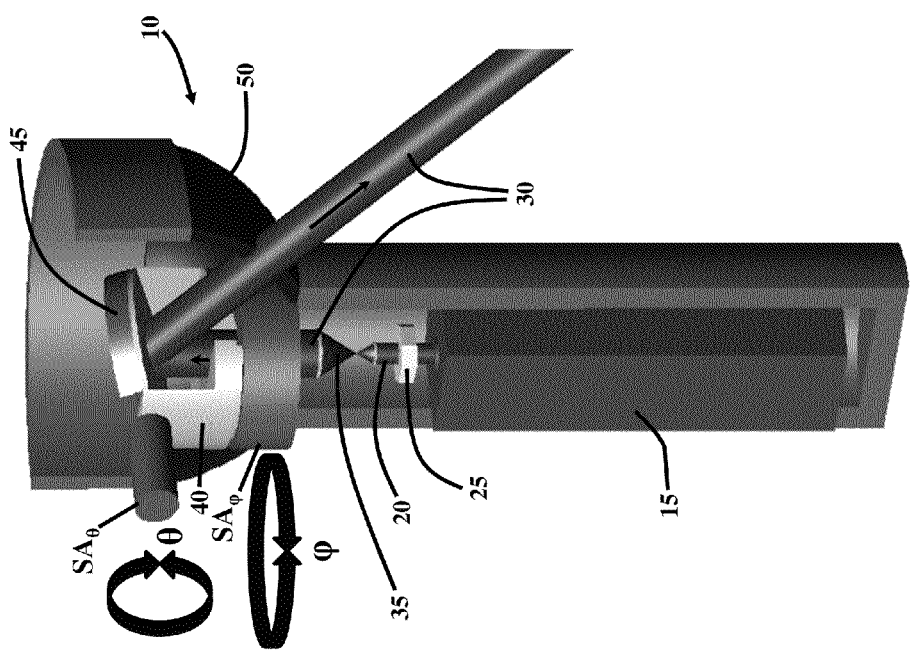
FIG. 2 illustrates a cut-away view of a laser transmitter component of a panoramic-imaging spectroradiometer (PANSPEC) surface contamination sensor model (PSCSM) according to an embodiment herein.
Figure 4:
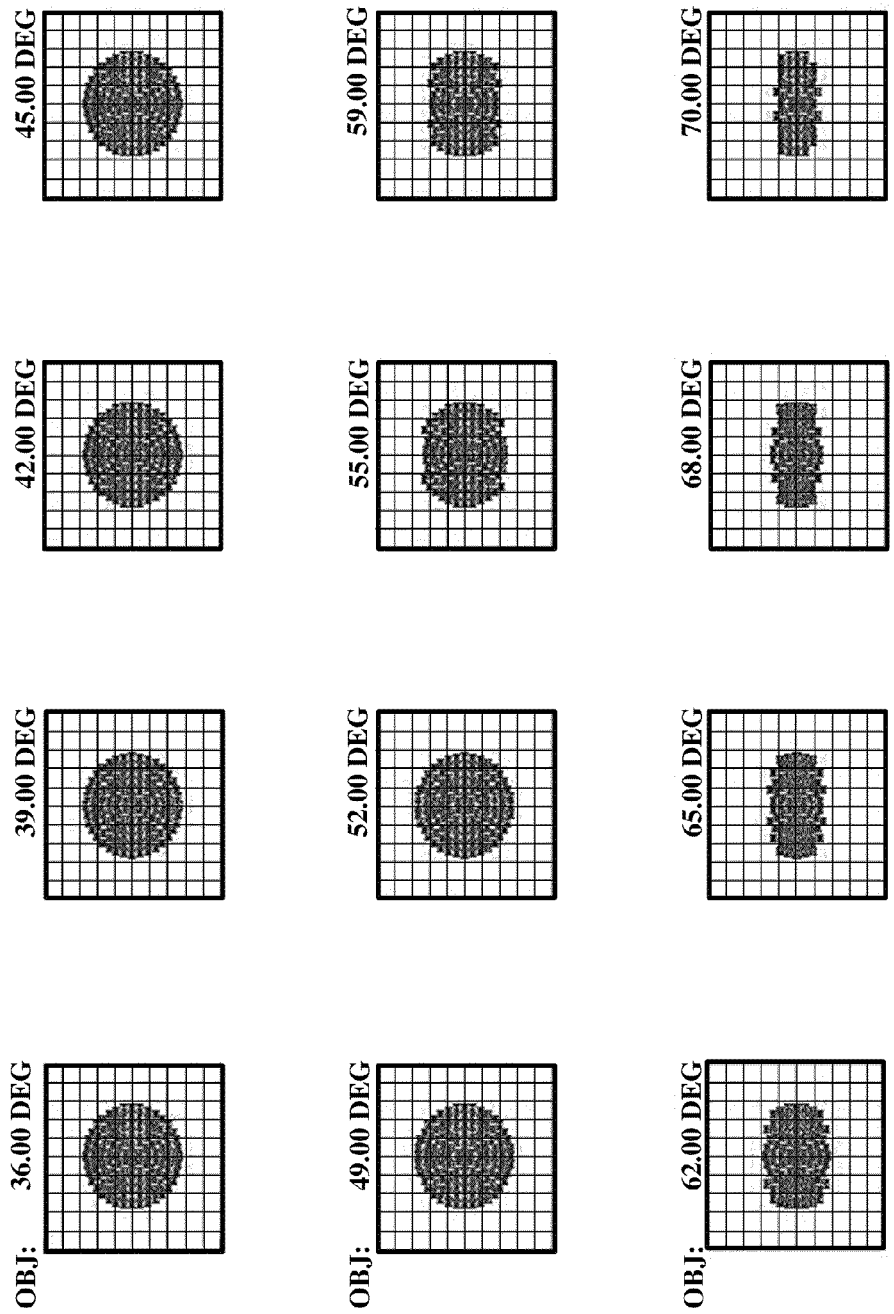
FIG. 4 illustrates graphical depictions of a focus performance of the collector-focuser optics group of the spectroradiometer receiver of FIG. 3 according to an embodiment herein.

FIG. 4, with reference to FIGS. 1 through 3, shows results of a focus performance of the collector-focuser optics component group 90 of the spectroradiometer receiver component 60 of the PANSPEC surface contamination sensor model PSCSM (of FIG. 3) at aperture stop 91c. The plots in FIG. 4 show focused rays originally launched from respective field angles $\sigma$ (numeric value of the angles given above each plot in FIG. 4) in the PSCCM's panoramic field of view for all middle infrared (MIR) wavelengths 8, 9, 10, 11, and 12 µm. In FIG. 4, the focal spot sizes are plotted as a function of the PFOV polar field angle $\sigma$ ranging from 37° to 70. Barrel distortion and field curvature are the dominant aberrations. Generally, as indicated in the plots of FIG. 4, increasing $\sigma$ increases (decreases) eccentricity (area) of focal spots. The root-mean-squared distance along the major axis of focal spots range from a maximum of 2003 µm at $\sigma=370$ to a minimum of 1664 µm at $\sigma=70°$.

Reflective Collimator:

Again, with reference to FIG. 3, the Schwarzchild collimator optics (SCO) component group 92 comprises of primary concave spheroid mirror 93a and secondary convex spherical mirror 93b. Mirror 93b outputs a condensed nearly parallel beam of MIR $\Omega$-radiance (e.g., iPFOV-beam) passed on to the interferometer, further described below.

Mirrors 93a, 93b have a common center of curvature (monocentric) which coincide at the center of AS 91c (i.e., they share a common focal point located at the center of AS 91c) and obey the following relationships given an infinite SCO conjugate focal length (f):

$$t_{9-10} = 2f, \qquad (2a)$$

$$p_9 = (5^{1/2} + 1)f, \qquad (2b)$$

$$p_{10} = (5^{1/2} - 1)f, \qquad (2c)$$

$$D_{10} = (5^{1/2} + 2)D_9, \qquad (2d)$$

$$d_{9\text{-}f} = (5^{1/2} + 2)f; \qquad (2e)$$

where $t_{9-10}$ is axial separation between mirrors 93a, 93b; $p_9$ is the (+) concave radius of curvature of mirror 93a; pin is the (−) convex radius of curvature of mirror 93b; $d_{9\text{-}f}$ is axial distance from the focal point of CF 90 to the vertex of mirror 93a, and $D_9(D_{10})$ is the clear aperture diameter of mirror 93a (mirror 93b). Accordingly, the SCO 92 is free of third order spherical aberration, coma, and astigmatism.

Virtual Stack Phased-Array Interferometer:

The solid-state VSPA interferometer 94 shown in FIG. 3 performs ultrahigh-speed (UHS) interferometry on the collimated iPFOV-beam incoming from the SCO 92. The VSPA interferometer 94 comprises front and back Ge linear-polarizers (not shown) and a VSPA bar PEM 96, which comprises a single stress-birefringence ZnSe crystal (not shown) with an array of ultrasonic-frequency piezoelectric transducers (PZTs) (not shown) bonded across the length of crystal. The PZT generates elastic waves (EWs) within the ZnSe medium), which is further described in U.S. Pat. No. 7,764, 415, the complete disclosure of which, in its entirety, is herein incorporated by reference. Behaviors of these induced EWs can be simulated such that the simulated model essentially emulates transients of the VSPA bar PEM 96 undergoing piezoelectric compression-relaxation in precisely timed and regulated cycles. Such transients induce a linear array of active resonance cells (ARCs) within the VSPA bar PEM medium resembling a virtual stack of oscillating phase retarder plates. The VSPA interferometer 94 includes an array of ARCs comprising EW wave reinforcement antinodes (A) and cancellation nodes (N) defining the ARC boundaries, whereby the vertical arrow represents the optical path of the lpPFOV-to-pmPFOV beam traveling through the bar 96. The VSPA bar PEM 96 attains maximum effective birefringence when all ARCs oscillate in phase; namely, when individual ARC birefringences add constructively. Under this condition, the spectroradiometer 60 of FIG. 3 exhibits its highest spectral resolution.

The Jones matrix (J-matrix) expresses the aggregate time-dependent stress birefringence behavior of VSPA interferometer 94 accordingly:

$$J = \begin{pmatrix} e^{i\delta/2}\cos^2\varepsilon + e^{-i\delta/2}\sin^2\varepsilon & 2i\sin 1/2\delta\cos\varepsilon\sin\varepsilon \\ 2i\sin 1/2\delta\cos\varepsilon\sin\varepsilon & e^{-i\delta/2}\cos^2\varepsilon + e^{i\delta/2}\sin^2\varepsilon \end{pmatrix}; \quad (3)$$

where $\delta$ is the time-dependent effective phase retardation (phase difference between extraordinary- and ordinary-eigenwaves of the lpPFOV-to-pmPFOV beam traced through the VSPA interferometer 94), and $\in$ is the azimuth angle of the effective fast axis of the VSPA bar PEM in piezoelectric transduction operating on those rays.

Refractive Imager and FPA

The imager component 100 of spectroradiometer 60 in FIG. 3 further comprises lens systems 95 including a front ZnSe biconvex/convex-concave lens doublet 95a, 95b, 95c, and 95d a back ZnSe convex-concave/convex-plano/convex-plano lens triplet 95f, 95g, 95h, 95i, 95j, 95k and a focal-plane detector (FPA) array 80. The Front lens group 95a-95d and the back lens groups 95f-95k are separated by air gap 95e. The lens elements per group touch on optical axis, and all lens surfaces are anti-reflection coated. The separation between FPA 80 and lens surface 95k is approximately 0.0050 mm, in one example, to allow for liquid nitrogen contact and 77 K cooling of the FPA's facing HgCdTe photoconductive pixel elements.

PSCSM Genetic Algorithm Optimization

A parametric optimization of laser transmitter 10 (of FIG. 2) and spectroradiometer receiver 60 (of FIG. 3) of the PSCSM integrated together is described below, starting from Hudson's systems engineering equation, which is further described in Hudson, Jr., R. D., "The analysis of infrared systems," *Infrared System Engineering*, pp. 417-421, John Wiley & Sons, New York, 1969, which is incorporated herein by reference:

$$R = [J \times \tau_a]^{1/2} \times [\pi^{1/2} EP \times NA \times \mathcal{T}]^{1/2} \times [D^*]^{1/2} \times [(\omega \times dF)^{-1/2} \times \mathcal{S}/\mathcal{N} \; (\tau_d, \Theta_{v(t)})^{-1}]^{1/2};$$

where R is the maximum detection range of the PSCSM in units of meters. The first bracket of Equation (4) specifies radiance of liberated TL fluxes pumped via the iPM-beam 30 of FIG. 2 (J in units of Wsr$^{-1}$) times atmospheric attenuation ($\tau_a$, which is unitless) of TL liberated radiances from suspect CCT to the entrance pupil (EP) of spectroradiometer 60 (FIG. 3). There is some control over the J-parameter, as it depends on energy, intensity, and polarization-modulation states of the iPM-beam 30. Also, $\tau_a$ is usually modeled from standard atmospheric transmission programs like HITRAN, however, it is set to unity for the relatively low detection ranges of a tactical defense system (TDS) 105 (of FIG. 5A). The second bracket of Equation (4) specifies parameters associated to the spectroradiometer: EP (units of meters) times numerical aperture (NA which is unitless) times J-throughput from Wr to FPA ($\mathcal{T} = t_{dome} r_{collector-focuser} r_{collimator} t_{interferometer} t_{imager}$, also unitless, where subscripted t and r symbols denote transmission and reflection coefficients of respective optic groups as shown in FIG. 3). There are nuances of design selection to consider here: increasing (decreasing) EP size increases (decreases) effective focal length thereby increasing (decreasing) FPA image size; NA rarely exceeds 0.5 in practical optical systems; and $t_{interferometer}$ is theoretically limited to a maximum value of 0.25. The third bracket of Equation (4) is a figure of merit of the liquid nitrogen cooled FPA called Detectivity (D* in units of mHz$^{1/2}$W$^{-1}$). D* equates to reciprocal noise equivalent power normalized to 8-12 µm optical spectral bandwidth of the spectroradiometer. The fourth bracket of Equation (4) specifies parameters associated to optics and electronics modules of the PSCSM-based prototype system: PFOV solid angle subtended onto the FPA ($\omega$ in sr units) times noise equivalent bandwidth of digital data acquisition system (dF in units of Hz) to the ½ power times reciprocal signal-to-noise ratio of coadded interferogram datasets ($\mathcal{S}/\mathcal{N}$ which is unitless). $\mathcal{S}/\mathcal{N}$ is functionally dependent on iPM irradiation dwell time on the CCT ($\tau_d$) and data acquisition rate $\Theta_{v(t)}$ of interferometer waveforms; namely, $\mathcal{S}/\mathcal{N}$ ($\tau_d, \Theta_{v(t)}$). Here, decreasing either $\omega$ or dF increases R to a 4th root power.

Figure 5:
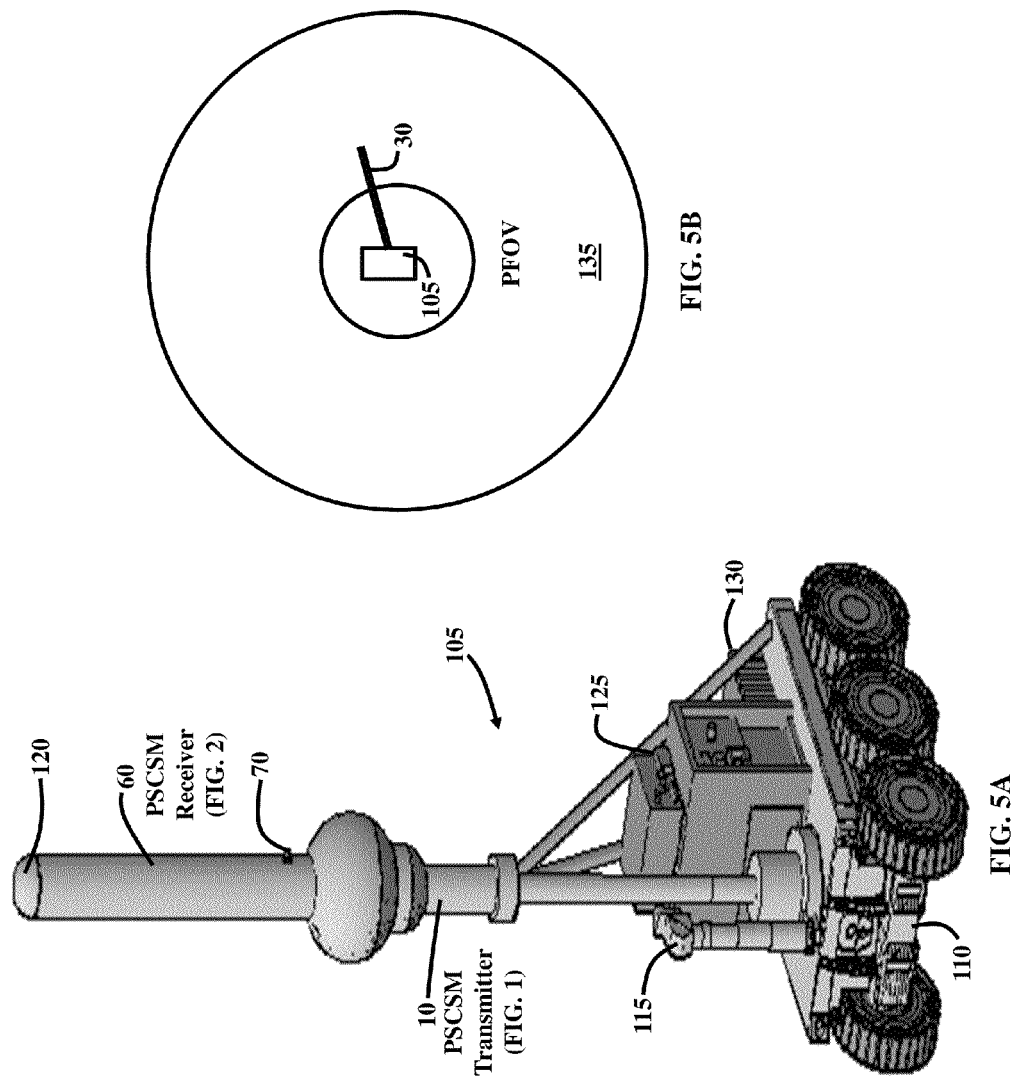
FIG. 5A illustrates a schematic diagram of a tactical defense system (TDS) mobilizing the PANSPEC according to an embodiment herein.
FIG. 5B illustrates a schematic diagram of a land area panorama of the spectroradiometer component of the PSCSM centered about the transceiver of the TDS according to an embodiment herein.

Tactical Defense System:

FIG. 5A, with reference FIGS. 1 through 4, illustrates a schematic diagram of a stage 2 tactical defense system (TDS) 105. The TDS 105 represents one example of integrating the PSCSM (transmitter 10 of FIG. 2 and receiver 60 of FIG. 3 combined together) on a robotic platform. This example is only one of several possible PSCSM-based sensor systems that implement contaminated terrain operational reconnaissance and facilitate a defensive guard against CWA surface contaminant hazards. The unmanned ground vehicle (UGV) 110 preferably utilizes a combination of electric traction motors and Li-ion or similar batteries for propulsion; as opposed to an internal combustion engine as the power source, since exhaust petroleum fumes from the latter power generator will mask the minute TL signature spectral metrics of subject surface contaminants in DHIMs. The TDS 105 may be configured to support ancillary systems such as a video camera 115 for surveying the UGV path of travel, a global positioning system (GPS) (not shown) for navigational guidance, a digital transceiver (not shown) for the reception/transmission of navigational/DHIM data (both GPS and transceiver electronics units are located under cap 120), electronics modules 125 governs various logistics of the TDS 105 movement and data handling, and a radio-frequency direct current power supply 130 for activating the iPM-beam 30 of FIG. 2. The Power supply 130 and waveguide laser 15 (of FIG. 2) may be fan-cooled. FIG. 5B, with reference to FIGS. 1 through 5A, shows the PFOV projection of the spectroradiometer 60 onto land 135 as viewed from above the TDS 105, and the iPM-beam 30 (of FIG. 2) sent to a suspect CCT area inside the PFOV land projection 135. The liquid nitrogen may not be a logistically sustainable resource in all environments (e.g., on the battlefield). Therefore, in an alternative embodiment, the FPA 80 may comprise an ambient nitrogen liquefier.

Figure 6:
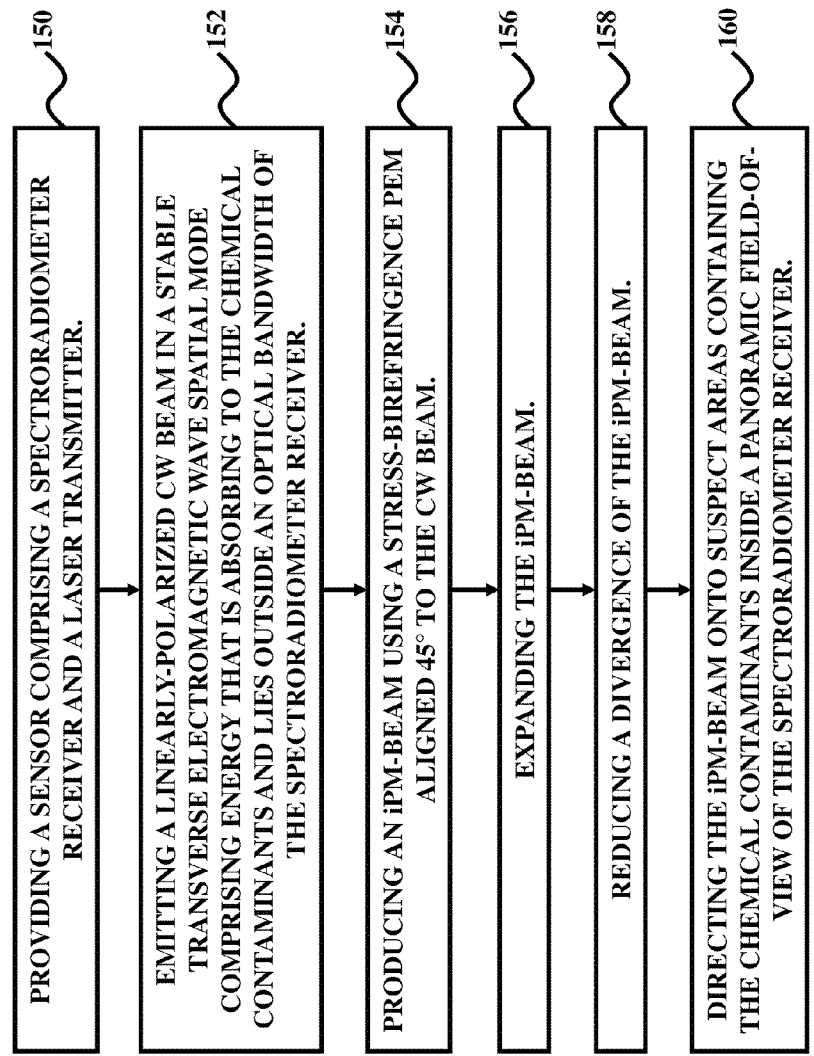
FIG. 6 is a flow diagram illustrating a method according to an embodiment herein.

FIG. 6, with reference to FIGS. 1 through 5B, illustrates a flow diagram of a method of detecting and imaging chemical contaminants according to an embodiment herein. The method comprises providing (150) a sensor comprising a spectroradiometer receiver 60 and a laser transmitter 10;

emitting (152) a linearly-polarized continuous-wave (cw) beam 20 in a stable transverse electromagnetic wave spatial mode comprising energy that is absorbing to the chemical contaminants and lies outside an optical bandwidth of the spectroradiometer receiver 60; producing (154) an incident polarization-modulation beam (iPM-beam 30) using a stress-birefringence photoelastic modulator (PEM) aligned 45° to the cw beam 20; expanding (156) the iPM-beam 30; reducing (158) a divergence of the iPM-beam 30; and directing (160) the iPM-beam 30 onto suspect areas containing the chemical contaminants inside a panoramic field-of-view of the spectroradiometer receiver 60.

The intensity of the iPM-beam 30 is below a first threshold that causes charring of an irradiated surface comprising the chemical contaminants, and the intensity of the iPM-beam 30 is at or above a second threshold that is required to generate sufficient thermal luminescence fluxes. The spectroradiometer receiver 60 comprises an internal chamber 75; an entrance window 65 that seals and protecting optic components within the internal chamber 75; and a vacuum pump-down valve 70 operatively connected to the internal chamber 75. The spectroradiometer receiver 60 further comprises a liquid nitrogen Dewar cryostat 85; and a focal-plane array detector 80 housed inside the Dewar cryostat 85 that produces interferogram waveforms of imaged panoramic field-of-view (PFOV) thermal luminescence flux rays. The spectroradiometer receiver 60 further comprises a collector optic component group 90 comprising a plurality of hyperboloid mirrors 91a, 91b. The spectroradiometer receiver 60 further comprises a Schwarzschild objective collimator optics component group 92 comprising a plurality of spherical mirrors 93a, 93b.

The spectroradiometer receiver 60 further comprises a stress-solid-state interferometer 94 comprising front and back linear polarizers (not shown) sandwiching a virtual stack phased-array (VSPA) bar photoelastic modulation (PEM) 96, wherein the VSPA bar PEM 96 comprises a single stress-birefringence ZnSe crystal (not shown) having an array of ultrasonic-frequency piezoelectric transducers (PZTs) (not shown) bonded across a length of the crystal, and wherein the VSPA bar PEM 96 is activated by the PZTs generating interferograms at ultrahigh-speed on collimated panoramic field-of-view light incoming from the Schwarzschild objective collimator optics component group 92 collected by the collector optic component group 90. The spectroradiometer receiver 60 further comprises a lens imager component group (e.g., lens systems 95) that images the PFOV rays of object space onto the focal plane array detector 80.

The method further comprises measuring and processing a dynamic pattern of absorptive-emissive middle infrared molecular signature spectra of analytes of the chemical contaminants. Additionally, the method further comprises performing a genetic algorithm optimization of the spectroradiometer receiver 60 and the laser transmitter 10.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A chemical imaging sensor for detecting and imaging chemical contaminants comprising analytes, said sensor comprising:
   a first component that performs irradiative transient heating;
   a second component that performs temperature nonequilibrium thermal luminescence spectroscopy, said second component comprising a spectroradiometer receiver, wherein said spectroradiometer receiver includes a collector optic component group comprising a plurality of hyperboloid mirrors, a Schwarzschild objective collimator optics component group comprising a plurality of spherical mirrors, and a stress-solid-state interferometer comprising front and back linear polarizers sandwiching a virtual stack phased-array (VSPA) bar photoelastic modulator (PEM), wherein said VSPA bar PEM comprises a single stress-birefringence ZnSe crystal having an array of ultrasonic-frequency piezoelectric transducers (PZTs) bonded across a length of the crystal, and wherein said VSPA bar PEM is activated by the PZTs generating interferograms at ultrahigh-speed on collimated panoramic field-of-view light incoming from said Schwarzschild objective collimator optics component group collected by said collector optic component group;
   a third component that performs differential hyperspectral imaging; and
   a fourth component that performs artificial neural networking,
   wherein the first, second, third, and fourth components combine to measure and process a dynamic pattern of absorptive-emissive middle infrared molecular signature spectra of said analytes.

2. The sensor of claim 1, wherein:
   said first component comprises a laser transmitter comprising a waveguide laser emitting a linearly-polarized continuous-wave (cw) beam in a stable transverse electromagnetic wave spatial mode comprising energy that is absorbing to said chemical contaminants and lies outside an optical bandwidth of said spectroradiometer receiver.

3. The sensor of claim 2, wherein said laser transmitter further comprises:
   a stress-birefringence photoelastic modulator (PEM) aligned 45° to said beam producing an incident polarization-modulation beam (iPM-beam); and
   a beam expander (BE) that expands said iPM-beam and reduces a divergence of said iPM-beam.

4. The sensor of claim 3, wherein said laser transmitter further comprises:
   a mirror;
   a raster scanner assembly (SA) that drives said mirror in azimuth angles φ and polar angles θ and directs said iPM-beam onto suspect areas containing said chemical contaminants inside a panoramic field-of-view of said spectroradiometer receiver; and
   a semi-shell entrance window that protects said waveguide laser, said PEM, said BE, said mirror, and said SA.

5. The sensor of claim 3, wherein an intensity of said iPM-beam is below a first threshold that causes charring of an irradiated surface comprising said chemical contaminants, and wherein said intensity of said iPM-beam is at or above a second threshold that is required to generate sufficient thermal luminescence fluxes.

6. The sensor of claim 1, wherein said spectroradiometer receiver further comprises:
an internal chamber;
an entrance window that seals and protects optic components within said internal chamber; and
a vacuum pump-down valve operatively connected to said internal chamber.

7. The sensor of claim 6, wherein said spectroradiometer receiver further comprises:
a liquid nitrogen Dewar cryostat; and
a focal-plane array detector housed inside said Dewar cryostat that produces interferogram waveforms of imaged panoramic field-of-view (PFOV) thermal luminescence flux rays.

8. The sensor of claim 7, wherein said spectroradiometer receiver further comprises a lens imager component group that images interferometrically-processed PFOV rays of object space from said VSPA bar PEM onto said focal plane array detector.

9. The sensor of claim 1, wherein said sensor is integrated on a robotic platform adapted to enable movement of said sensor for operational use.

10. A method of detecting and imaging chemical contaminants, said method comprising:
providing a sensor comprising a spectroradiometer receiver and a laser transmitter, wherein said spectroradiometer receiver includes a collector optic component group comprising a plurality of hyperboloid mirrors, a Schwarzschild objective collimator optics component group comprising a plurality of spherical mirrors, and a stress-solid-state interferometer comprising front and back linear polarizers sandwiching a virtual stack phased-array (VSPA) bar photoelastic modulator (PEM), wherein said VSPA bar PEM comprises a single stress-birefringence ZnSe crystal having an array of ultrasonic-frequency piezoelectric transducers (PZTs) bonded across a length of the crystal, and wherein said VSPA bar PEM is activated by the PZTs generating interferograms at ultrahigh-speed on collimated panoramic field-of-view light incoming from said Schwarzschild objective collimator optics component group collected by said collector optic component group;
emitting a linearly-polarized continuous-wave (cw) beam from said laser transmitter in a stable transverse electromagnetic wave spatial mode comprising energy that is absorbing to said chemical contaminants and lies outside an optical bandwidth of said spectroradiometer receiver;
producing an incident polarization-modulation beam (iPM-beam) using a stress-birefringence photoelastic modulator (PEM) aligned 45° to said cw beam;
expanding said iPM-beam;
reducing a divergence of said iPM-beam; and
directing said iPM-beam onto suspect areas containing said chemical contaminants inside a panoramic field-of-view of said spectroradiometer receiver.

11. The method of claim 10, wherein an intensity of said iPM-beam is below a first threshold that causes charring of an irradiated surface comprising said chemical contaminants, and wherein said intensity of said iPM-beam is at or above a second threshold that is required to generate sufficient thermal luminescence fluxes.

12. The method of claim 10, wherein said spectroradiometer receiver further comprises:
an internal chamber;
an entrance window that seals and protects optic components within said internal chamber; and
a vacuum pump-down valve operatively connected to said internal chamber.

13. The method of claim 12, wherein said spectroradiometer receiver further comprises:
a liquid nitrogen Dewar cryostat; and
a focal-plane array detector housed inside said Dewar cryostat that produces interferogram waveforms of imaged panoramic field-of-view (PFOV) thermal luminescence flux rays.

14. The method of claim 13, wherein said spectroradiometer receiver further comprises a lens imager component group that images the PFOV rays of object space onto said focal plane array detector.

15. The method of claim 10, further comprising measuring and processing a dynamic pattern of absorptive-emissive middle infrared molecular signature spectra of analytes of said chemical contaminants.

16. The method of claim 10, further comprising performing a genetic algorithm optimization of said spectroradiometer receiver and said laser transmitter.

* * * * *